(12) United States Patent
Nassief

(10) Patent No.: US 7,592,327 B2
(45) Date of Patent: Sep. 22, 2009

(54) ASTHMA/ALLERGY THERAPY THAT TARGETS T-LYMPHOCYTES AND/OR EOSINOPHILS

(76) Inventor: Nida Abdul-Ghani Nassief, P.O. Box 4606, Doha, Qatar (QA)

( * ) Notice: Subject to any disclaimer, the term of this patent is extended or adjusted under 35 U.S.C. 154(b) by 1651 days.

(21) Appl. No.: 09/944,564

(22) Filed: Sep. 4, 2001

(65) Prior Publication Data

US 2002/0061841 A1    May 23, 2002

(30) Foreign Application Priority Data

Mar. 2, 1999    (GB) .................................. 9904777.1

(51) Int. Cl.
*A61K 31/715*    (2006.01)
(52) U.S. Cl. ................ 514/54; 514/23; 514/62
(58) Field of Classification Search ............... 536/18.7, 536/123.1, 123.12, 124; 514/25, 42, 54, 514/62

See application file for complete search history.

(56) References Cited

OTHER PUBLICATIONS

Ernst Mutschler et al. Drug Actions: Basic Principles and Therapeutic Aspects, CRC Press, 1995, pp. 408-409, 429-430, 611.*

John Walton et al. The Oxford Medical Companion, Oxford University Press, 1994, p. 171.*
Sanchez Palacios A. et al. Allergol Immunopathos (Madr), 1992, vol. 20 (1), pp. 35-39 (English Abstract).*
Annesi-Maesano I. Allergy (1999), vol. 54, Suppl. 57, pp. 7-13.*

* cited by examiner

*Primary Examiner*—Patrick T Lewis
(74) *Attorney, Agent, or Firm*—Meyer, Unkovic & Scott LLP; David G. Oberdick; Debra Z. Anderson

(57) ABSTRACT

A pharmaceutical composition for the treatment and/or prophylaxis of diseases caused by type I hypersensitivity reactions consisting essentially of Glicophosphopeptical, or pure *Nigella Sativa* seeds, in a concentration which stimulate Th1 lymphocytes and selectively switch-off the eosinophilic airway inflammation A method of treatment of allergy using Th1 stimulating agents, to be administered to a mammal such as human in need of such treatment in a shot of 5 days only, resulted in significant decrease in symptom score started day 3, and in sputum eosinophils by day 14, followed by long-term clinical remission of a mean of 6 months.

The BCG-like Th1 stimulation is also used in treating diseases in which the body defensive mechanism is a Cell Mediated Immunity, including viral infections, as but not limited to influenza and common cold, Chronic and recurrent urinary tract infection, pelvic inflammatory diseases as neuroimmune appendicitis, cancer, crohns disease and facial palsy.

10 Claims, No Drawings

ASTHMA/ALLERGY THERAPY THAT TARGETS T-LYMPHOCYTES AND/OR EOSINOPHILS

TECHNICAL FIELD

This invention is generally directed to the fields of medicine and pharmacology, and specifically directed to a pharmaceutical composition for the treatment of asthma/allergy, consisting essentially of Glycosphosphopeptical, or as an equivalent pure *Nigella sativa* seeds, which is active to stimulate T-helper lymphocytes type 1 therefor selectively switching-off the eosinophilic inflammation, also treating viral respiratory tract infections (flue & influenza), other viral infection, urinary tract infection, pelvic inflammatory diseases in particular neuroimmune appendicitis, cancer, crohns disease and facial palsy.

REFERENCES

Are listed according to their appearance in the text after the abstract.

BACKGROUND ART

Asthma is the epidemic of the new millennium. Despite the increase in our knowledge, the morbidity, mortality and prevalence of asthma and other allergic diseases are increasing as shown by WHO statistics. (1)

Barnes J December 1999, review the current state of antiasthma therapy, over the past 10 years there have been striking improvement in the treatment of asthma largely as a result of the earlier and more widespread use of inhaled corticosteroids. The developments of new treatments for asthma has proved difficult, although several immunologic approaches are undergoing preclinical and clinical assessment. Antileukotrienes are the only new class of drugs to treat asthma that have been introduced in the past 25 years, but their efficacy is somewhat limited and unpredictable, as compared with that of inhaled corticosteroids. (2)

The main disadvantages associated with inhaled corticosteroids is that it should be used on day-to-day bases, alternate day steroid therapy is unable to control the disease (British National Formulary). Four weeks treatment with recommended dose of corticosteroids is associated with significant increase in peak expiratory flow rate, and decrease the need for rescue salbutamol use in asthmatic subjects, but was not associated with large reductions in markers of eosinophilic inflammation, bronchovascular permiability, or mucus hypersecretion. Alternative therapies for corticoseroid-dependant asthma, such as methotrexate, cyclosporine and oral gold, are problematic and have high incidence of adverse effect. (2)

2-Immunological therapy: in the form of allergen immunotherapy is the only therapeutic modalities which have the potential to modify the natural course of the disease, hence, immunotherapy is a preventive and curative treatment, mostly by inducing immune deviation (upregulation of a distinct subset of Th0/Th1 cells). It is a cumbersome therapy.

There is accordingly an outstanding need for an effective and convenient means for treating and/or preventing type I IgE-mediated hypersensitivity reactions, including asthma, in mammals.

1—Glycophosphopeptical: The present inventor has, surprisingly, found that a short-term administration of Glycophosphopeptical (Glicofosfopeptical) to patients suffering from asthma is capable of treating and/or preventing asthma, Glycophosopeptical is marketed under the trade names "IMMU-NOFERON" and "INMUNOFERON" drug by Industrial Farmaceutica Cantabria, S.A. (Spain), Glycophosopeptical is a GLUCOMANNAN from *Candida utillis* to be used as an immnostimulant for oncology, secondary immunodeficiency, and stimulating cell mediated immunity. It is not indicated for the treatment of diseases caused by type I hypersensitivity and asthma defined Of particular interest was the clinical effect of Glicophosphopeptical treatment in chronic bronchitis patients, which resulted in significant increases in the number of monocytes as well as their phagocytic and chemotactic activity. The depressed number of natural killer cells was reversed to near their levels in young healthy adults. These observations help to explain how glycophosphopeptical aids in the restoration of natural cellular immunity and its possible application as an adjuvant to bacterial & viral vaccines as well as in the treatment chronic bronchitis. (3)

Inmunoferon enhances the activities of early-type interferon inducers and natural killer cells, although it is not an interferon inducer by itself. (4)

Intraduodenal administration of a phosphorylated glycomannan-protein fraction of the cell wall of *Candida albicans* resulted in a significant increase in Interferon response in the abdominal lymph in rabbits immunized against *Candida albicans*. Antiviral activity was absent in plasma in all cases. (5)

Glocomannan-containing antiobesity pharmaceuticals due to delayed food digestion in the stomach. (6)

Pharmaceutical application of Konjac glucomannan. (30)

The immunologic enhancement activity of dicarboxy glucomannan was evaluated in vitro by determining glucose conumption and beta-glucuronidase activity in cultured macrophages. (31)

2—*Nigella sativa*: Herbs are highly desired as a "natural" way to treat a disease. Some preparations have been known for literally thousands of years while others are just being discovered to have curative effects

*Nigella sativa*, also known as black cumin, is a well-known herb, and its seeds are widely available for use as a spice or condiment. *Nigella sativa* is folk medicines, treating many diseases including many with respiratory symptoms.

Medenica R D (1995) disclose the use of *N. sativa* as a medicinal treatment, providing an anticancer remedy and treatment which has, as its active ingredient, the extract of the plant *N. sativa*. When used properly, the medicament of the present invention is useful in treating cancer at a concentration which is effective to destroy cancer cells in a patient, preventing toxicity of anticancer drugs in human body, and in increasing immune function, and as a growth factor for bone marrow in hematopoiesis. Also directed to a method for protecting the normal cells from cytopathic effects of virus. The effective dose is about 30 grams of the extract per day, the concentration of the extract from *Nigella sativa* is sufficient to reduce the presence of one or more factors normally present in the human body, the factors being selected from the group consisting of interferon inhibitor factor and lymphokine inhibitor factor. (7)

Shawkat (1989) describe an extract solution and herbal mixture for treatment of Hepatitis-B and Hepatitis-C, containing *Nigella sativa* L in a mixture with 9 other herbs. (8)

The following studies are considered relevant to the relation between *N. sativa* and asthma: Sayed 1980: The oil is used in the treatment of asthma, respiratory oppression and coughs. The active principal, nigellone, has been isolated from the volatile oil fraction and is reported to be useful in the treatment of bronchial asthma. (9)

Mahfouz M and El-Dakhakhny M 1960: The chemical and pharmacological properties of the new anti-asthmatic drug, nigellone. (10)

El-Tahir et al 1993: The respiratory effect of the volatile oil of the black seed (*Nigella sativa*) in guinea-pig: elucidation of the mechanism (s) of action. (11)

Aqcl M B 1992 The calcium antagonistic effect of the volatile oil of *Nigella sativa* seeds. (12)

Reicex M, Brandt W 1985: The relaxant effects of *N sativa* on tracheal and ileal smooth muscles of the guinea-pig. (13)

Elkadi A and Kandil O, 1987: *Nigella sativa* and Immunity Its Effects increase CD4 (helper) T cell population. (14)

Boskababy & Shahabi, 1997: Bronchiodilatory and Anti-cholinergic effects of *Nigella sative*. (15)

Mutabagani & El-Mahdy, 1997: A study of the Anti-inflammatory activity of *Nigella sativa*. (16)

3—*Bacillus* Calmette Guerin (BCG): is a strain of mycobacterium used to induce immunity to tuberculosis by stimulating Cell Mediated Immunity mediated by T lymphocytes (Th1). The relation of BCG vaccination to asthma is a debate.

BCG has also been used as a therapeutic agent in the treatment of cancer, inducing Cell Mediated Immunity when given as a systemic or intralesionl injection, (17, 18, 19). BCG is also used to treat viral warts that are resistant to other forms of therapy T lymphocyte stimulation in culture is an in vitro correlate of cell mediated immunity. An evaluation of the effect of *N. sativa* on T lymphocytes in culture indicated that the water extract, chloroform extract and oil layer of *N. sativa* each show similar activity to preparations of a known standard antigen purified protein derivative from BCG.

Measles or rubella infection can cause tuberculin positive patients to revert temporarily and become tuberculin negative. (20) Therefore viral infections in general, benefits from BCG-like Th1 stimulation as described by this invention.

4—The role of cytokines in allergic inflammation and cell recruitment:

Currently, IgE production is under the control of Interleukiens produced by T-helper 2 lymphocyte, allergy is clearly a Th2 disease.

Eosinophilia is a consistent and characteristic feature of airway mucosa of late-phase asthmatic response to allergen. IL-3, IL-5 and GM-CSF are eosinnophil active cytokine.

Asthma is an inflammatory mediator soup. (21)

Th1 cells develop in the presence of a large range of antigens associated with delayed hypersensitivity response like tuberculosis, sarcoidosis, leprosy, and viruses, generates predominantly IFN gamma which inhibits the differentiation and production of cytokines by Th2 and vice versa. (21, 22, 23, 24, 25)

5—My novel concept in immunopathology of allergy.

A normal person is in a state of "Tolerance to Environmental Antigen, TEA".

Pre-inflammatory phase of allergy is controlled by Th1 cells, and it's cytokine interferon. This is based on my discovery that interferon is a potent Eosinophil Chemotactic Factor.

TH1 suppression is the cause of allergy. Manifested by low serum interferon in acute asthmatic attacks. (26, 27)

Th1 stimulation is capable of selectively switch-off the eosinophilic airway inflammation, normalizing serum interferon This can be achieved by using a novel class of asthma therapy, which is the subject of this invention. "days" therapy with a BCG-like Th1 stimulation ⇒long term clinical remission

DISCLOSURE OF THE INVENTION

The present invention is introducing a new class of anti-allergy/anti-asthma therapy that target the pre-inflammatory phase of the allergic reaction being defined by the present inventor as "Th1 lymphocytes" and its cytokine "interferon".

This present invention provides a pharmaceutical composition and treatment of asthma/allergy, consisting essentially of Glycophosphopeptical, or an equivalent pure *Nigella sativa* seeds, which is active to stimulate T-helper lymphocytes type 1 therefor selectively switching-off the eosinophilic inflammation.

The present inventor has, surprisingly, provided a method of treatment for patients suffering from asthma/allergy, administering Glycophosphopeptical to a mammal such as human in need of such treatment a shot of 5 days only, to get a, significant decrease in symptom score started day 3, and in sputum eosinophils by day 14, followed by long-term clinical remission of a mean of 6 months, therefore this method is capable of treating and/or preventing the disease.

The present invention is specifically directed to a method of treatment of diseases caused by type I IgE-mediated hypersensitivity reaction comprising the administration to a mammal such as a human in need of such treatment, of an effective dose of Th1 stimulating agents The present invention is specifically typified by a dosage regimen as a characterizing feature, administering to a patient suffering from a chronic disease a short-term therapy of 1-30 days, preferably 5 days, of a Th1 stimulating agent, to get a long-term clinical remission of months as a result of selective switching-off of the eosinophilic inflammation.

The present invention is specifically directed to the use of Th1 stimulating agents for the preparation of an agent for the treatment and/or prophylaxis of diseases caused by type I IgE-mediated hypersensitivity reaction, such as extrinsic, intrinsic or mixed asthma, allergic and perennial rhinitis, allergic conjunctivitis, chronic urticaria, atopic dermatitis, and/or laryngeal oedema, to be administered to a mammal such as human in need of such treatment.

The present invention is still further directed to the use of Th1 stimulating agent, for the treatment and/or prophylaxis of diseases caused by type 1 IgE-mediated hypersensitivity reaction for administration to a mammal such as a human.

The present invention is specifically directed to a medicament characterized in that said Th1 stimulating agent comprises Glycophosphopeptical in free base form, or a pharmaceutically acceptable salt or hydrate, or any pharmacologically active form.

In addition the present invention is specifically directed to a medicament characterized in that said Th1 stimulating agent comprises the pure form of *Nigella sativa* seeds, as an equivalent.

The present invention claims a medicament which is adapted and/or packaged for periodic administration to said mammal in doses over a period of 3-30 days, preferably 5 days in doses at least once daily up to ten times/day. The said medicament is characterized in that each one of said doses comprises up to 2000 mg of said active agent, preferably about 200-1000 mg, of said active agent, adapted for oral administration to said mammal in capsules, or tablets, or lozenges, or as a powder, or a suspension, or a syrup. Also a medicament which is adapted for topical administration to said mammal such as a human, in the form of eye or nasal drops or ointment, also skin or vaginal cream or ointment. Each of the above preparation are to be produced as a kit comprising a medicament as claimed in any of claims 1-9 packaged in separate doses for periodic administration to said mammal such as a human, contains written or printed instructions.

The use of Th1 stimulating agents in the treatment of allergy/asthma is dependent on the fact that interferon is an in vivo Eosinophilic Chemotactic Factor, and that serum interferon and Th1 lymphocytes are controlling the pre-inflammatory phase of allergic reaction.

The method of treating a chronic asthma and allergy using 5 days schedule is based on that the recommended dose of Th1 lymphocytes stimulating agent is sufficient to selectively switch-off the eosinophilic inflammation in the patient's airway.

Th1 lymphocytes stimulating agents, are capable of stimulating T lymphocytes in culture, comparable to Purified Protein Derivative of BCG, as a standard agent that stimulates Cell Mediated Immunity.

Use of Th1 stimulating agents had been extended to involve the preparation of an agent for the treatment and/or prophylaxis of diseases characterized by a body immune defensive mechanism is Cell Mediated Immunity as viral respiratory tract infections such as, but not limited to influenza and common cold, other viral infections.

Additionally the present invention provide a method of treatment of viral respiratory tract infections such as, but not limited to influenza and common cold, other viral infections comprising the administration to a mammal such as a human in need of such treatment, of an effective dose of Th1 stimulating agents.

The present invention is directed to the use of Th1 stimulating agents for the preparation of an agent for the treatment and/or prophylaxis of diseases characterized by a body immune defensive mechanism is Cell Mediated Immunity as acute and recurrent urinary tract infection, pelvic inflammatory diseases such as but not limited to neuroimmune appendicitis, and cancer.

Additionally the present invention provide a method of treatment of as acute and recurrent urinary tract infection, pelvic inflammatory diseases such as but not limited to neuroimmune appendicitis, and cancer comprising the administration to a mammal such as a human in need of such treatment, of an effective dose of Th1 stimulating agents.

Surprisingly the present invention has been extended to involve a method of treatment of crohns disease comprising the administration to a mammal such as a human in need of such treatment, of an effective dose of Th1 stimulating agents in order to stimulate Cell Mediated Immunity, also the use of Th1 stimulating agent, for the treatment of crohns disease to be administered to a mammal such as a human in need of such treatment.

The present invention also provide a method of treatment of facial palsy comprising the administration to a mammal such as a human in need of such treatment, of an effective dose of Th1 stimulating agents, and to using Th1 stimulating agent, for the treatment of facial palsy to be administered to a mammal such as a human in need of such treatment.

The present invention is providing a shot therapy of 1-20 days, preferably 5 days for type I hypersensitivity reaction, of particular interest but not limited to the chronic corticosteroid-dependent allergy and asthma. It provides a steroid saving activity.

The present invention is providing a shot therapy of 1-20 days, preferably 5 days for chronic diseases, the therapeutic effect of which lasts for a mean of 6 months. Such therapeutic schedule had never been known in medical practice.

INDUSTRIAL APPLICABILITY

Manufacturing a pharmaceutical preparation to provide a therapy for mammals including humans for the treatment of asthma and allergy, also a Th1 stimulating and Cell Mediated Immunity stimulating remedy for viral diseases urinary tract infection, pelvic inflammatory disease, crohns disease, and facial palsy. Containing the active ingredient Glycophosphopeptical or the pure seeds of *Nigella sativa* as an equivalent. May be administered orally as capsules, tablets, slow release preparations, or liquid preparation, also parenteral preparations. Topical medicaments for nasals, eyes, or skin and vaginal preparations.

BEST MODE FOR CARRYING OUT THE INVENTION

The present invention was conceived during October 1993, after an experiment of nature that happened to the inventor. Being sever asthmatic her asthma was relived after certain health incident. As an immunologist she linked the incident with interferon. This is considered as Stage I.

Stage II: The discovery that interferon is a potent in vivo Eosinophil Chemotactic Factor.

Stage III: A marketed drug immunoferon (glycophosphopeptical), indicated for diseases unrelated to type 1 hypersensitivity, was linked with allergy in a novel way (depending on the above observation), using it in a non-routine indication and dosage.

In order to prove its utility and reduction to practice, a double-blind placebo controlled clinical trial was designed. 120 subjects with different types of allergy were chosen and divided into two groups, matched for age, sex, and severity of the allergic condition after an informed consent into the study. Group 1 including 60 patients treated with inmunoferon Group 2 including 60 patients treated with placebo.

1—Diseases involved include seasonal allergic rhinitis, allergic conjunctivitis, chronic urticaria, asthma, and laryngeal edema.

2—The duration of treatment, the total dose received and the schedule of therapy were verified to find the best method of treating various allergies. Glycophosphopeptical was given in addition to the conventional therapy. The full course of 15 g total dose, was divided over 5 days administering 1000 mg 8 hourly.

Alternatively a single dose of 500 mg glycophosphopeptical, Single dose of 1000 mg glycophosphopeptical, or one day therapy. Any of this treatment can be repeated on need.

3—The patients were self-evaluated daily regarding symptoms severity over the preceding 24 hours. A global overall evaluation of treatment efficacy was made by the doctor according to daily notes and findings during clinical examination, at intervals, depending on patient's attendance.

4—The response was recorded according to, the time of onset, and the degree of a noticeable symptomatic improvement.

5—All the patients included was having sever symptoms which are sufficiently troublesome to interfere with daily activity or nocturnal sleep.

The final global improvement rating includes:

Markedly improved: almost approaching normal condition.

Moderately improved: having mild symptoms.

Slightly improved: having frequent troublesome symptoms but not interfering daily activity or sleep.

Unchanged: remains as in the pre-treatment condition.

Difficult to evaluate no conclusion could be reached.

Three main symptoms were chosen for each of the conditions studied, they were:

In seasonal allergic rhinitis: running nose, frequency of sneezing, nasal obstruction.

Allergic conjunctivitis: redness of the eye, itching, swelling.

Chronic urticaria: frequency of recurrence, distribution on the body, severity of itching.

Asthma: dyspnoea, wheeze, and cough.

Laryngeal edema: fullness in the throat, hoarseness of the voice, inspiratory difficulty.

During the course of Glycophosphopeptical treatment, 80% of the treated patients showed a significant decrease in symptom score in the treated group compared to placebo. The onset of action is within 8 hours, 50% reduction in symptom score was noticed by day 3, reaching maximum in day 7. Such symptomatic improvement is totally unexpected particularly in patients with allergic rhinitis, asthma and laryngeal edema.

Above all, is the observation that a long-term effect for this short-term therapy was noticeable! During glycophosphopeptical treatment it was possible to stop all other forms of therapy, including steroids. Hence the present invention is useful as a treatment and/or prevention of allergy and asthma.

Side effects: few are mentioned in the manufacturer's leaflet, glycophosphopeptical is not contraindicated for asthma or allergy, no other side effects were noticed during this short course of therapy.

Stage IV: Nine patients age range 36-72 with chronic severe asthma of a duration ranging between 1-32 years, all of whom were on a maximal dose of broncodilators (as recommended by the manufacturer) and maintenance corticosteroids, were chosen on account of poor response to conventional treatment, were treated according to the present invention administering glycophosphopeptical orally as in the following design of study:

Day 0: pre-treatment period, is considered as base line, patients were receiving maximal dose of broncodilators (as recommended by the manufacturer) and maintenance corticosteroids.

Day 1: is the beginning of glycophosphopeptical treatment, 1000 mg glycophosphopeptical is administered to the patient 8 hourly, for 5 days (total of 15 grams or 30 capsule) over the whole study period.

The patients were asked to refrain from taking their conventional drugs and steroids when possible.

The effects of treatment with Glicophosphopeptical on the subjects were assessed according to the following assessment criteria:

1—Symptom triad of cardinal symptoms including dyspnoe, cough and sputum. The symptoms were scored daily as follows:

| Dyspnoea: | No dyspnoea | Score = 0 |
| --- | --- | --- |
| | Mild on doing physical activity | Score = 1 |
| | Moderate at rest | Score = 2 |
| | Severe constant annoying dyspnoea | Score = 3 |
| Cough: | No cough | Score = 0 |
| | Mild cough at times | Score = 1 |
| | Moderate frequent annoying cough | Score = 2 |
| | Severe constant distressing cough | Score = 3 |

-continued

| Sputum: | No sputum | Score = 0 |
| --- | --- | --- |
| | Small amount expectorated with ease | Score = 1 |
| | Tenacious moderate amount | Score = 2 |
| | Plenty causing severe mucus-related symptoms | Score = 3 |

2—Composite Symptom Scoring:

This is an indication of therapeutic effectiveness in improving the patients' global assessment. The sum of the score is 39. Scorings on a level of 0-3 being awarded for each of the following symptoms, the score was recorded daily:

Cough frequency, cough severity, audible wheeze, Tachycardia, Chest discomfort, Nocturnal dyspnoea disturbing sleep, Ability to walk up stairs, Ability to talk and laugh, Stress incontinence caused by the cough, Necessity to take days off work, Psychological well-being, Hospitalization rate, and need for conventional drugs.

The percent reduction in symptom scoring was calculated according to the following formula:

(base-line score−follow-up score)/(base-line score−1)%.

3—Pulmonary Function Test:

Was carried out to assess "the alteration in airway flow and bronchial patency resulting from glycophosphopeptical treatment" by measuring changes in FEV1, PEFR, FEF25% (alveolar), FEF50% (small airways), FEF75% (large airways).

4—Sputum Examination:

Hypersecretion of heavy mucus or sputum, resulting in mucus-related symptoms, is characteristic of asthma. The eosinophil levels in the sputum are generally found to correlate with the severity of the disease. The sputum produced by the patients during the course of glycophosphopeptical therapy was consequently observed for changes both at a macroscopic and a microscopic level Macroscopically, there was a tremendous decrease in the amount of sputum and a change in its visco-elastic properties. The sputum became thin and easily expectorated. Changes were noticeable after day 3 of the therapy, and within 10 days the patients were free from mucus-related symptoms.

Serial microscopic sputum examinations for the percentage of eosinophils in relation to other inflammatory cells were performed. Samples of sputum from the patients were smeared onto slides, fixed with methanol, and stained using haematoxylin-eosin. A total of 300 inflammatory cells (lymphocytes, polymorphonuclear leukocytes, macrophages, and basophils) were counted in each slide, and the percentage of eosinophils in this count was calculated.

The percent reduction in sputum eosinophils was calculated according to the following formula:

(base-line count−follow-up count)/(base-line count−1) %.

5—Serum samples to carry out relevant tests as serum interferon level, total serum IgE, and serum cationic protein.

Results of stages III and IV:

The total number of asthmatic patients treated with glycophosphopeptical is: 25 patients in stage III+10 patients in stage IV+20 patients during the year 1999.

The total number of controls: 35 patients.

The percent reduction in symptom score was 65-100%

The reduction in symptom score as a result of glycophosphopeptica therapy is shown in table 1

TABLE 1

| Mean symptom score | Glycophosphopeptical (N = 55) | Placebo (N = 35) |
|---|---|---|
| Day 0 | 34.5 | 33.2 |
| Day 3 | 20.5 | 27.3 |
| Day 7 | 9.66 | 29.7 |
| Day 14 | 5.8 | 30.6 |
| Day 21 | 4.4 | 31.4 |

Improvement was noticeable by day 3 of the therapy, and reached a maximum by 7-10 days of therapy Patient compliance is very good, because this treatment is capable of achieving the confidence of the chronically ill patient with some psychological element from the disease.

Tapering of oral and inhaled corticosteroid was possible, this treatment have a steroid saving effect. In addition rescue use of inhaled bronchodilators as measured by the daily number of puffs required was significantly reduced.

The increment in airway patency is the result of the selective switching-off of the eosinophilic inflammatory process.

There was a decrease in the percentage of sputum eosinophils with glycophosphopeptical therapy from 80% to less than 10% within the first two weeks of glycophosphopeptical therapy. In addition the use of student t test shows significant decrease in the number of sputum eosinophils after glycophosphopeptical therapy as compared to pre-treatment number.

Long-term follow up:

After the end of the course of glycophosphopeptical therapy, during which a total of 30 capsules of glycophosphopeptical were administered to each subject, no further glycophosphopeptical was administered. Over the next 23 months, the subjects' symptoms were regularly assessed on the following criteria:

Frequency of attacks of shortness of breath, coughing, wheezing, and sputum

Daily activity

Disturbance of sleep

Need for traditional forms of asthma therapy

Rate of hospitalization

Asthmatic attacks were infrequent and mild, being manifested only in some shortness of breath, with mild coughing and small amounts of sputum. Traditional forms of asthma therapy were required only when the subjects were suffering from colds. At least eight out of the ten subjects were able to lead a normal lifestyle during the long-term follow up period, with no nocturnal or early morning dyspnoea. It was found that the hospitalization rate for each subject during the long-term follow up period was on average reduced from several times per month (prior to glycophosphopeptical therapy) to 1-3 times per year.

During the follow-up period, microscopic analysis of the subjects' sputum indicated a reduction in eosinophil levels to only 5-10% of the total inflammatory cells. This level was maintained except during exacerbation, when eosinophil levels rose to 30-40% of total inflammatory cells.

Conclusion: Glycophosphopeptical is an agent that can be used in treating asthma of all types and severity, allergic/perennial rhinitis, and other allergies. This short-term therapy produce Long-term effect Stage V: is the discovery that *Nigella sativa* (also known as fitch, black cumin, or love-in-the-mist) is an equivalent to glycophosphopeptical. The use of the pure seeds of *Nigella sativa* for the preparation of an asthma and allergy agent in a concentration which was found to perform substantially the same function in substantially the same way to obtain substantially the same results as with glycophosphopeptical.

For the present invention the pure herbal seeds are first dried and crushed or ground to a powder, preserving its' pharmacological activity as a BCG-like Th1-stimulating agent. This powder is presented or packaged in individual doses, contained in sachets or capsules, for oral administration to a patient. Each dose of *N. sativa* comprises 400-800 mg of the powder. During treatment doses are administered to the patient orally three times daily.

For children the dose is 45-180 mg/Kg body weight preferably 80 mg/Kg.

Analysis of composite symptom score using the Kruskal-wallis one-way analysis of variance by ranks shows significant changes.

Recent clinical trials show that this invention is successful as a treatment for chrons disease, the dose is given as an aqueous extract three times daily. It was capable of switching-off the Th1 inflammation.

In addition *Nigella sativa* and glycophosphopeptical are useful in the treatment of facial palsy, possibly because facial palsy is possibly a complication of a viral infection.

Measurements of Lymphocyte Activation and Proliferation in Culture, after Stimulating Them by *Nigella sativa* Extracts, Comparing it to Purified Protien Derivitive (PPD) of *Bacillus Calmette Gurene* (BCG).

This test is an in vitro technique for the measurement of cell mediated immunity. Lymphocytes are stimulated in vitro, by placing the culture in contact with a known concentration of various mitogens, antigens, cytokines, or antibodies. Lymphocytes became metabolically active, transformed into lymphoblast, cell division results in increased DNA synthesis. $^3$H-thymidine incorporation is used as an indicator of that synthesis. The radioactivity increases in proportion to the number of lymphoblasts formed in culture, and is measured by liquid scintillation spectrometer.

Antigen stimulation using an antigen as PPD, is characterized by a limited number of responding T cells, The first step in this response is the interaction of antigen specific T-cells with antigen-presenting cells. After recognition of the specific antigen, the T cell undergoes a series of physiologic changes resulting in its transformation to a lymphoblas, culminating in cell division. Maximum stimulation occurs within 6-7 days. The stimulation index for antigen is over 3.

The stimulation index: is the relative increase in $^3$H thymidine incorporation into DNA in the presence of mitogen and antigen, compared to the control without the addition of mitogen and antigen.

Stimulation index=E/C=(Mean cpm of cells with mitogen or antigen−background)/(mean cpm of cells with media−background) (29).

In this study: Water, chloroform extracts, and the top layer of extraction from *Nigella sativa* seeds, were compared to PPD (Purified Protein Derivative of *Bacillus* Calmette Gurene [BCG]) as a standard antigen, that can be used for immunotherapy in humans Preparation of *N. sativa* Extract
- gram of *N. sativa* seeds was finely grounded to a powder.
- In a volumetric burette, 100 cc chloroform and then 100 cc distilled water were placed. Then the powder of *N. sativa* was added, and the burette was capped.
- Manual shaking was performed for ½ hour, the burette hanged in holder overnight.
- Next day the suspension was settled into 3 separate layers inside the burette: lower Chloroform, middle water, and a top oily layer. Each layer contains different soluble constituents from *N. sativa* seeds. Each layer, as stock, was collected in a different container and kept at 4° C. After 10 days, each layer was tested separately for its ability to stimulate lymphocytes in culture.

Procedure:
1. All cell manipulation was performed at room temperature, using sterile techniques.
2. Blood sample from healthy normal females, BCG vaccinated, 30-45 years of age was drawn fresh by venipuncture and anticoagulated with 20 IU heparin/ml
3. Whole blood was layered gently on 15 ml lymphoprep trying not to disturb the interface, then the tube was capped.
4. Centrifuge at 1500 RPM for 30 minutes at 18° C.
5. With a Pasteur pipette and the attached bulb depressed the plasma was discarded. The lymphocyte band removed to be used in the following steps.
6. The lymphocytes was washed with phosphate buffers saline (PBS), and resuspended to a final concentration of $1 \times 10^6$ cell s/ml in RPMI medium containing penicillin and streptomycin.

A dose response test was performed to determine the optimal dose for stimulation of this batch of lymphocytes.
7. ml of cell suspension was added to all the wells of microculture plate.
8. ml antigen was added to different plates in triplicates as follows:
    PPD antigen at concentration of 0, 10, 20, 30, 40, 50 microgram/ml.
    *N. sativa* extract prepared from stock, diluted to ½, ¼, ⅛, 1/16, 1/32
9. The plates were then incubated for 1-9 days at 37C in an atmosphere of 5% CO2 in air.
10. 20 hours before harvesting, 50 microliter of 20 microcuri/ml were added to each well, and the plates re-incubated
11. For harvesting, the plates were chilled and each well rinsed individually into cold saline and cells were filtered through glass-fiber filters.
12. The filters were then washed with cold 5% trichloroacetic acid, then with methanol, placed in scintillation vials and allowed to dry.
13. When dry add 10 ml of scintillation fluid (5 g PPO, 0.1 g dimethyl POPOP, 100 ml toluene) were added to each vial and the vial counted in a liquid scintillation counter.

Time response test: The above steps 7-13 were repeated, using optimal dose of antigen from the dose response test (PPD 30 microgm/ml, *N. sativa* extract diluted from stock ⅛) to detect the time needed for maximal incorporation of $^3H$ thymidine.

Results

Dose-response test for antigen stimulation (PPD), optimal concentration (30 microgm/ml).

Time-response for antigen stimulation (PPD) using optimal concentration (30 microgm/ml), maximum response occurred on day (5) of culture.

Dose-response test for *N. sativa* extract, optimal dilution from the stock of water, chloroform, and top layer is ⅛.

Time-response test for *N. sativa* extract (water, chloroform, and top layer) ⅛ dilution from stock, maximum response occurred on day (5) of culture.

Conclusion *N. sativa* extracts has got a stimulatory effect on lymphocytes in culture, as shown in table 2

TABLE 2 the stimulation index of PPD and *N. sativa* extract.

| | PPD. | *N. sativa* Water extract | *N. sativa* Chloroform extract | *N. sativa* Top layer |
|---|---|---|---|---|
| Time response test | 4.6 | 4.4 | 4.3 | 4.3 |
| Dose response test | 4.5 | 5.2 | 4.5 | 4.5 |

REFERENCES

1- Help our children breath. Press release WHO v.95"/December 1998. World health organization press office, WHO web site: www.who.ch/
2- Barnes P J, The New England Journal of Medicine. Dec. 23, 1999. Vol. 341, No. 26:
3- Villarubia, V. G.; Moreno, Koch M. C.; Calvo, C.; Gonzaiez, S.; Alvarez-Mon, M. The immunosenescent phenotype in mice and humans can be defined by alterations in the natural immunity reversal by immunomodulation with oral AM3. The immunosenescent phenotype in mice and humans can be defined by alterations in the natural immunity reversal by immunomodulation with oral AM3. Immunopharmacol. Immunotoxicol, 1997;19(1): 53-74.
4- Moya P, Baixeras E, Barasoain I. Inmunoferon enhances the activities of early-type interferon inducers and natural killer cells. Immunopharmacol. Immunotoxicol. 1987, 9 (2-3); 234-56.
5- Paulesu L, Bocci V, Pessina G P, et al. Interferon induction in rabbits after intraduodenal administration of a phosphorylated glycomannan-protein fraction of the cell wall of *Candida albicans*. Immunol. Lett. 1991, 27 (3); 231-5.
6- Glocomannan-containing antiobesity pharmaceuticals. Shimizu, Hideki (Shimizu Chemical K. K., Japan). Jpn. Kokai Tokkyo Koho JP 01224320 A2 7 Sep. 1989 Heisei, 5 PP. (Japan) CODEN: JKXXAF. CLASS: ICM: A61K031-715. ICS: A23K001-16: A61K035-78. APPLICATION: JP 88-48345, March 1988. DOCUMENT TYPE: Patent CA Section: 63 (Pharmaceuticals) Section cross-reference(s): 1.
7- Medenica Rajko, D. *Nigella sativa* as a medicinal treatment. International Application No: PCT/US94/09660, International Filling Date: 25 Aug. 1994, International Publication No: WO 95/05839, International Publication Date: 2 Mar. 1995.
8- SHAWKAT T. Extract solution and herbal mixture for treatment of hepatitis. U.S. Pat. No: 5,648,089. Date of Patent Jul. 15, 1997.
9—Sayed M D. Traditional medicine in health care. J Ethnopharmacol 1980 March; 2 (1): 19-22
10- Mahfouz M and El-Dakhakhny M: chemical and pharmacological properties of the new anti-asthmatic drug, nigellone. Egypt Pharm Bul 1960: 42: 411-424.
11- El-Tabir K E H, Ashour M M S, a al; The respiratory effect of the volatile oil of the black seed (*Nigella sativa*) in guinea-pig: elucidation of the michanism (s) of action. Gen Pharmacol 1993; 24: 1115-1122. (non relevant).
12- Aqcl M B: The calcium antagonistic effect of the volatile oil of *Nigella sativa* seeds. Jordar Ser B 1992; 119-133.
13- Reicex M, Brandt W: Relaxant effects on tracheal and ileal smooth muscles of the guinea-pig. Arzneim Forsch/Drug Res 1985; 35: 408-414.

15- Boskababy & Shahabi. Bronchiodilatory and Anticholinergic effects of *Nigella sative* . . . . *Iranian Journal of Medical Science* (1997), 23(3-4), 127-133.
16- Mutabagani & El-Mahdy. A study of the Anti-inflammatory activity of *Nigella saliva* . . . Saudi Pharmaceutical Journal (1997), 5(2) 110-113.
17- Morton D L. Local therapy with biologic agents, Intralesional therapy: 691. Biologic therapy of cancer 1995 J.B. Lippincott Company, Philadelphia.
18- Witt P L. Chemically defined immunomodulators and interferon inducers: 787. Biologic therapy of cancer 1995. J.B. Lippincott Company, Philadelphia.
19- Akporiaye E T, Hersh E M. Cancer vaccines: clinical applications, Immune adjuvants: 635. Biologic therapy of cancer 1995. J.B. Lippincott Company, Philadelphia.
20- ABPI, DATA SHEET, COMPENDIUM. 1995-1996: 555. Publisher: datapharm Publications Limited.
21- Bjornsdottir, Cypcar D M. Asthma: An inflammatory mediator soup. Allergy 1999; 54: 55-61.
22- Romagnani S. The Th1/Th2 paradigm and allergic disorders. Allergy 1998; 53 Suppl 46: 12-15. $7^{th}$ International symosium on immunological, chemical and clinical problems of food allergy, Italy 4-7 Oct. 1998.
23- Holgate S T, Come J, Jardieu P, et al. Treatment of allergic airways disease with anti-IgE. Allergy 1998: 53 supplement 45 30 years with IgE: An international symposium on basic and clinical aspects of atopic allergy Stockholm, 1-2 Sep. 1998: 83-88.
24- Palma Carlos A G, Palma Carlos M L, Santos M Conceicao, Melo Alcinda. Cytokines and asthma. J Invest Allergol Clin Immunol 1997 September-October; 7(5) J of Invest Allergol Clin Immunol Vol 7 No 5 Interasma '97 Annual Meeting Western Europe Chapter. Dec 3-5 1997.: 270-273.
25- Menz G, Ying S , Durham S R. Molecular concepts of IgE-initiated inflammation in atopic and nonatopic asthma. Allergy 1998; 53 suppl 45 30 years with IgE: An international symposium on basic and clinical aspects of atopic allergy Stockholm, 1-2 Sep. 1998: 15
26- Lebedin-Y S; Raula-L A; Chuchalin-A G. Serum levels of inteleukin 4, inteleukin 6 and interferon-gamma following in vivo isotype-specific activation of IgB synthesis in humans. Int-Arch-Allergy-Appl-Immunol 1991; 95 (1)92-4.
27- Jankowska-R, Szalaty-H, Malolepszy-J, Sypula-A, Zielinska-Jenczylik-J. Production of interferon by leukocytes from patients with atopic and nonatiopic asthma. Arch-Immunol-Ther-Exp-Warsz. 1988; 36 (5): 523-6.
28- WHO Position Paper Allergen immunotherapy: therapeutic vaccines for allergic diseases. Allergy 1998; 53 Supplement 44: 12-13.
29- Harbeck R J, Giclas P C. Lymphocyte stimulation with mitogen and antigens: 211-219. Diagnostic Immunology Laboratory Manual 1991. Raven press.
30- Jin Miaozhen; Yang, Fan. Pharmaceutical application of Konjac glucomannan. Guangdong Yiyao xueyuan xuebae, 10 (1), 1-3 (Chines) 1994.
CODEN: GYYXEI. ISSN: 1005-2607. DOCUMENT TYPE: Jornal General review CA section: 63 pharmaceuticals.
31- Ohya, Ynichi; Ihara, Kenji; Murata, Jun-ichi; Ouchi, Tatsuro. Biodegradation and immunological enhancement activity of dicarboxy-glucomannan having recognizable branched saccharide residues. Adv. Sci. Technol., 10 (Intelligent Materials and Systems), 273-280 (English) 1995. CODEN: ASETE5. DOCUMENT TYPE: Journal CA Section: 1 (Pharmacology) Section cross-reference(s): 44.

The invention claimed is:

1. A method of treatment of allergy and asthma patients in need of such treatment, comprising administering a pharmaceutical composition consisting essentially of glycophosphopeptical in multiple doses for a short term treatment period of 1-20 days to induce a remission of several months during which further treatment is not necessary.

2. The method of claim 1 wherein the short term treatment period lasts 3-5 days.

3. The method of claim 1 wherein the glycophosphopeptical is administered in doses up to 2000 mg.

4. The method of claim 1 wherein the glycophosphopeptical is administered in doses of 200-1000 mg.

5. The method of claim 1 wherein the glycophosphopeptical is administered in doses at least once daily up to 10 times daily.

6. The method of claim 1 wherein the glycophosphopeptical is administered orally as capsules, tablets, lozenges, a powder or a syrup.

7. The method of claim 1 wherein the glycophosphopeptical is administered topically in the form of eye or nasal preparations such as drops or ointment, or skin or vaginal preparations such as cream and ointment.

8. The method of claim 1 for the treatment of patients suffering from extrinsic asthma, intrinsic asthma or mixed extrinsic/intrinsic asthma.

9. The method of claim 1 for the treatment of patients suffering from allergic and perennial rhinitis, allergic conjunctivitis, chronic urticaria, atopic dermatitis or laryngeal oedema.

10. The method of claim 4 of treating patients suffering from chronic corticosteroid-dependent allergy and asthma.

* * * * *